(12) United States Patent
Kojima et al.

(10) Patent No.: US 7,370,965 B2
(45) Date of Patent: May 13, 2008

(54) OPHTHALMOLOGICAL MEASURING APPARATUS

(75) Inventors: Atsushi Kojima, Hamamatsu (JP); Yuki Egawa, Chofu (JP); Takayoshi Suzuki, Hamamatsu (JP)

(73) Assignee: Kowa Company Ltd. (JP)

( * ) Notice: Subject to any disclaimer, the term of this patent is extended or adjusted under 35 U.S.C. 154(b) by 128 days.

(21) Appl. No.: 11/258,815

(22) Filed: Oct. 26, 2005

(65) Prior Publication Data

US 2006/0087615 A1  Apr. 27, 2006

(30) Foreign Application Priority Data

Oct. 27, 2004  (JP) ............................. 2004-311688
Jun. 1, 2005  (JP) ............................. 2005-160808

(51) Int. Cl.
*A61B 3/10* (2006.01)
*A61B 3/00* (2006.01)

(52) U.S. Cl. ...................................... 351/205; 351/246

(58) Field of Classification Search ........ 351/205–206, 351/246
See application file for complete search history.

(56) References Cited

U.S. PATENT DOCUMENTS

| | | | | |
|---|---|---|---|---|
| 5,548,355 A | * | 8/1996 | Iki | 351/212 |
| 5,815,240 A | * | 9/1998 | Iki | 351/212 |
| 2004/0252276 A1 | * | 12/2004 | Nanjo et al. | 351/206 |
| 2005/0018135 A1 | * | 1/2005 | Maeda et al. | 351/206 |
| 2005/0117118 A1 | * | 6/2005 | Miller et al. | 351/246 |

\* cited by examiner

*Primary Examiner*—Scott J. Sugarman
*Assistant Examiner*—DaWayne A Pinkney
(74) *Attorney, Agent, or Firm*—Adams & Wilks

(57) ABSTRACT

An ophthalmological measuring apparatus has a display that displays a digital image of an imaged ocular fundus of a subject eye. A specifying device specifies an arbitrary point on the displayed digital image. An extracting device extracts from the displayed digital image an image region whose brightness value is higher than a brightness value of the specified arbitrary point.

19 Claims, 11 Drawing Sheets

FIG. 2

ESTIMATED VALUES OF THE RADIUS OF CURVATURE OF THE FRONTAL CORNEAL SURFACE

| DIOPTER | EYE AXIAL LENGTH (mm) | | | | | | | | |
|---|---|---|---|---|---|---|---|---|---|
| | 18 | 20 | 22 | 24 | 26 | 28 | 30 | 32 | 34 |
| 10 | 6.07 | 7.14 | 8.36 | 9.77 | 11.40 | | | | |
| 8 | 5.86 | 6.85 | 7.97 | 9.24 | 10.68 | 12.33 | | | |
| 6 | 5.67 | 6.59 | 7.61 | 8.76 | 10.04 | 11.49 | | | |
| 4 | 5.49 | 6.35 | 7.29 | 8.33 | 9.48 | 10.76 | 12.19 | | |
| 2 | 5.32 | 6.12 | 6.99 | 7.94 | 8.98 | 10.12 | 11.37 | 12.76 | |
| 0 | 5.16 | 5.91 | 6.72 | 7.59 | 8.53 | 9.55 | 10.65 | 11.86 | |
| −2 | | 5.72 | 6.46 | 7.26 | 8.12 | 9.04 | 10.02 | 11.09 | 12.23 |
| −4 | | 5.53 | 6.23 | 6.97 | 7.75 | 8.58 | 9.46 | 10.40 | 11.41 |
| −6 | | 5.36 | 6.01 | 6.70 | 7.41 | 8.17 | 8.96 | 9.80 | 10.69 |
| −8 | | 5.21 | 5.81 | 6.45 | 7.11 | 7.80 | 8.51 | 9.27 | 10.05 |
| −10 | | 5.06 | 5.62 | 6.21 | 6.82 | 7.46 | 8.11 | 8.79 | 9.49 |

FIG. 5

RETINAL IMAGING RANGE (mm): Model A/50 degrees

| DIOPTER | EYE AXIAL LENGTH (mm) | | | | | | | | |
|---|---|---|---|---|---|---|---|---|---|
| | 18 | 20 | 22 | 24 | 26 | 28 | 30 | 32 | 34 |
| 10 | 9.23 | 10.37 | 11.38 | 12.39 | 13.39 | | | | |
| 8 | 9.32 | 10.48 | 11.50 | 12.52 | 13.54 | 14.55 | | | |
| 6 | 9.42 | 10.59 | 11.62 | 12.66 | 13.69 | 14.71 | | | |
| 4 | 9.51 | 10.70 | 11.75 | 12.79 | 13.83 | 14.87 | 15.91 | | |
| 2 | 9.61 | 10.81 | 11.87 | 12.93 | 13.99 | 15.04 | 16.08 | 17.13 | |
| 0 | 9.71 | 10.93 | 12.00 | 13.07 | 14.14 | 15.20 | 16.26 | 17.32 | |
| -2 | | 11.04 | 12.13 | 13.21 | 14.29 | 15.37 | 16.44 | 17.51 | 18.58 |
| -4 | | 11.16 | 12.26 | 13.36 | 14.45 | 15.54 | 16.62 | 17.71 | 18.79 |
| -6 | | 11.28 | 12.40 | 13.50 | 14.61 | 15.71 | 16.81 | 17.91 | 19.00 |
| -8 | | 11.40 | 12.53 | 13.65 | 14.78 | 15.89 | 17.00 | 18.11 | 19.24 |
| -10 | | 11.52 | 12.67 | 13.80 | 14.93 | 16.06 | 17.18 | 18.30 | 19.33 |

OPHTHALMOLOGICAL MEASURING APPARATUS

BACKGROUND OF THE INVENTION

1. Field of the Invention

The present invention relates to an ophthalmological measuring apparatus, and more particularly relates to an ophthalmological measuring apparatus that derives an actual distance on an ocular fundus based on a fundus image on a screen.

2. Description of the Prior Art

With fundus cameras, there is a demand to be able to view a photograph taken of a fundus and derive the size of a lesion part, the distance on the retina from the lesion part to the macula lutea, and the like. This is because Japanese Patent Publication No. 2000-60893, for example, discloses a photodynamic therapy (PDT) that treats age-related macular degeneration by irradiating a spot of the lesion part with a laser beam, and the actual distance on the retina is needed in this therapy in order to form an appropriate laser spot. When providing treatment by irradiating a lesion part with a laser spot in this manner, it is a problem if the spot size of the beam to be shone is either too large or too small, and there is consequently a demand to form a laser spot of a prescribed size with high precision. Generally, it is said that the optimal spot size is the lesion maximum diameter plus 1 mm. Consequently, the maximum diameter of the lesion part must be accurately measured beforehand, and the beam spot size must be set to a size of the lesion part maximum diameter plus 1 mm.

The distance between prescribed points on a retina has conventionally been derived by assuming that the diopter of the affected eye is 0 diopters, setting a conversion magnification for determining the actual length from the taken image based on the specifications of the optical system of the fundus camera, applying that magnification to a taken image, and then deriving the length on the retina. Actually, there are individual differences that naturally arise in optical systems of fundus cameras, so that such differences must be eliminated. For this purpose, a model eyeball whose eye diopter is 0 diopters is used, and the conversion magnification is determined by using a simulation to derive a length at which the retina can be fully imaged in the mask when imaging the model eyeball with the fundus camera.

Nevertheless, the diopters of actual subject eyes vary, and the eye axial lengths, the corneal curvatures, and the like, also vary. In addition, there is a problem in that the operation of focusing the fundus camera varies the focal length (magnification) of the fundus camera, as is noted by Japanese Patent Publication No. 2003-225208. Accordingly, it is conventionally problematic to accurately derive the actual distance on an ocular fundus because there is considerable error in the distance calculation, which is based on the assumption that the affected eye diopter is 0 diopters.

On the other hand, it is necessary to recognize the position of the lesion part on the retina and to accurately derive the distance of that portion in order to form a laser spot having the appropriate size as mentioned above. To detect the position of the lesion part, a technology as disclosed in Japanese Patent Publication No. 1980-49778 is used that extracts the contour of an image based on, for example, brightness because the brightness at the lesion part varies.

In addition, Japanese Patent Publication No. 1994-125876 discloses a method wherein the papilla part and a pale part are also extracted from the fundus image based on the brightness, and Japanese Patent Publication No. 2003-310555 discloses a method wherein the average brightness of the papilla part is derived and the lesion part is thereby specified from the average brightness thereof.

It is therefore an object of the invention to provide an ophthalmological measuring apparatus capable of accurately deriving the actual distance on an ocular fundus.

It is another object of the invention to provide an ophthalmological measuring apparatus capable of easily specifying a prescribed region within a fundus image and capable of accurately measuring that region.

SUMMARY OF THE INVENTION

According to the present invention, an ophthalmological measuring apparatus comprises an imaging optical system for acquiring a digital image of an ocular fundus; means for displaying the digital image of the imaged ocular fundus; means for specifying points on the image displayed, and means for calculating an actual distance between the specified points on the ocular fundus based on optical imaging parameters in the imaging optical system and part or all of the diopter of a subject eye, the eye axial length of the subject eye and the corneal curvature of the subject eye.

Furthermore, an ophthalmological measuring apparatus according to the invention comprises an imaging optical system for imaging a digital image of an ocular fundus with a mask disposed at the position conjugate to the ocular fundus to determine an imaging range thereof; means for displaying the imaged digital image; means for specifying points on the image displayed; storage means for storing the size of the mask on the ocular fundus that is calculated at least in accordance with subject eye parameters that affect the imaging magnification; and means for calculating an actual distance between the specified points on the ocular fundus based on the mask size that is read out from the storage means, a coordinate distance of the mask on a display screen, and a coordinate distance between the specified points on the display screen.

The present invention is capable of accurately measuring an actual distance on an ocular fundus because it derives the actual distance on the ocular fundus based on eye parameters that affect the imaging magnification, such as the diopter of a subject eye, the eye axial length of the subject eye and the corneal curvature of the subject eye, and based on the information of the imaging optical system, such as fluctuations in the imaging magnification of the imaging optical system, and fluctuations in the imaging magnification produced by movement of a focusing lens along the optical axis for compensation for differences in the diopter of the subject eye.

An ophthalmological measuring apparatus according to the invention further comprises means for displaying a digital image of an imaged ocular fundus; means for specifying an arbitrary point on the image displayed; and means for extracting a region whose brightness value is higher than the brightness value of the point specified.

With the present invention, a region of high brightness can be extracted from prescribed points specified by a user, and it is therefore possible to easily specify the region of a lesion part having high brightness on a retina compared with other locations. The extracted region is used to provide a minimum circle that includes the outer circumference of the extracted region. The diameter of the minimum circle or the surface area thereof is corrected in accordance with the optical imaging parameters in the optical system and the subject eye parameters that affect the imaging magnification to provide the accurate actual distance of the circle diameter on the ocular fundus. This allows the laser spot to be accurately formed in conformance to the actual size of the lesion part of the subject eye.

Further features of the invention, its nature and various advantages will be more apparent from the accompanying drawings and following detailed description of the invention.

BRIEF DESCRIPTION OF THE DRAWINGS

FIG. 2 is a table that shows the association between the diopter, the eye axial length, and the corneal radius of curvature.

FIG. 5 is a table that shows the association between the diopter, the eye axial length, and the retinal imaging range.

DESCRIPTION OF THE PREFERRED EMBODIMENTS

Figure 1:
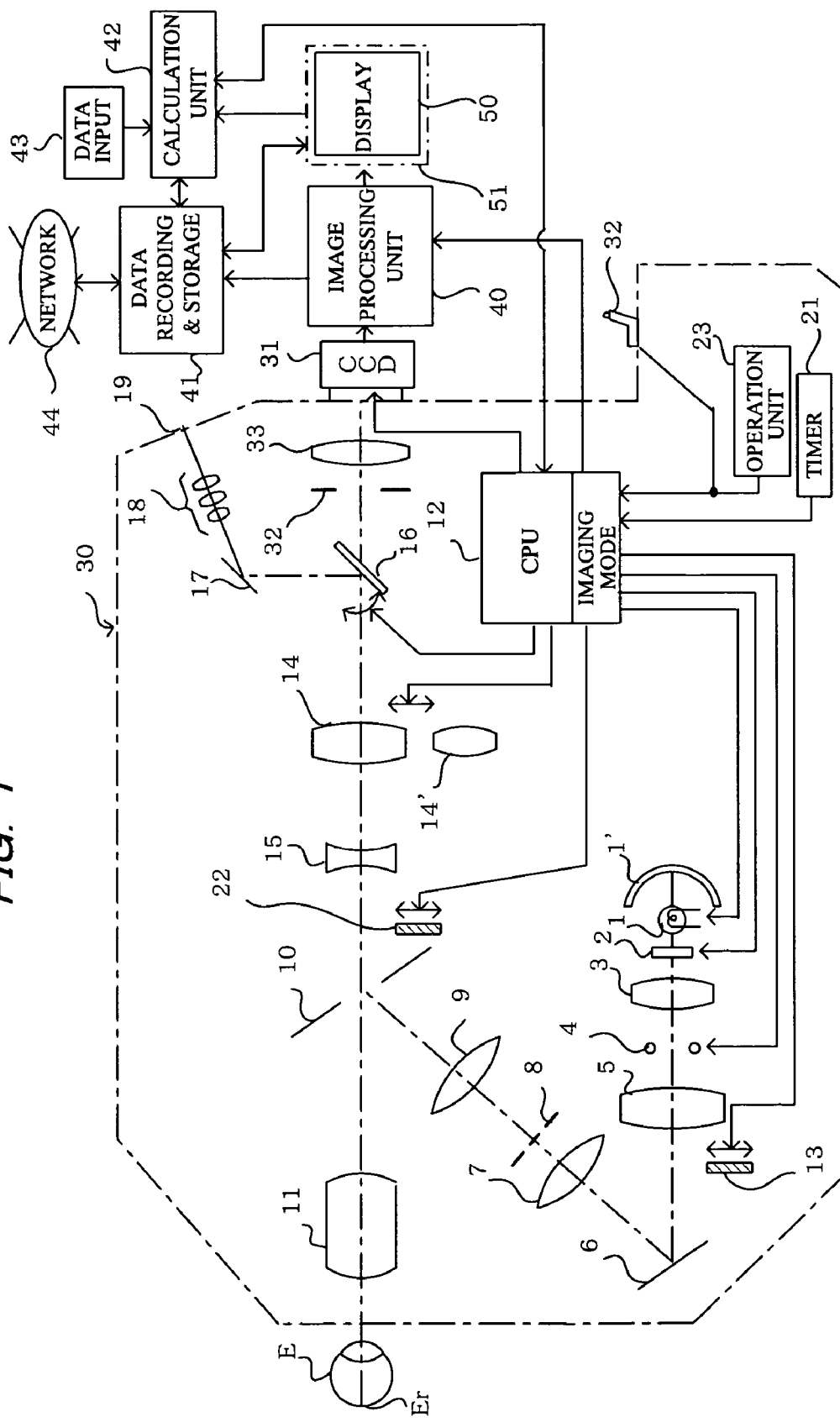
FIG. 1 is a block diagram showing the constitution of the ophthalmological measuring apparatus of the present invention.

FIG. 1 shows a fundus camera unit 30 that is used to take a fundus image as a digital image. The light from an illumination lamp 1 and a mirror 1' passes via a filter 2, a condenser lens 3, a strobe lamp 4, and a condenser lens 5, is reflected by a fully reflecting mirror 6, passes via a lens 7, a ring slit 8 for forming a ring illumination and a relay lens 9, is reflected by an apertured fully reflecting mirror 10 having an aperture at its center, passes via an objective lens 11, and impinges on an ocular fundus Er of a subject eye E.

The reflected light from the ocular fundus Er is received via the objective lens 11, passes via the aperture of the apertured fully reflecting mirror 10, passes through a focusing lens 15 and a variable power lens 14 (14'), and impinges on a return mirror 16. During observation, the return mirror 16 is inserted at the position shown in the figure. The fundus image is guided to an observation part 19 via a mirror 17 and a lens group 18, and an examiner then observes the ocular fundus. During imaging, or when the actual distance on an ocular fundus is measured with the present invention, the return mirror 16 is removed from the optical path, and the fundus image is received by a CCD camera (photoelectric conversion device) 31 via a mask 32 for determining the imaging range of the ocular fundus and via an image forming lens 33. The ocular fundus is then imaged as a digital image. The mask 32, having a circular aperture, and the light receiving surface of the CCD camera 31 are both disposed at positions conjugate to the eye fundus. In this imaging optical system, the focusing lens 15 is movable along the optical axis in order to adjust for fluctuations in the imaging position due to the diopter of the subject eye.

During fluorography, an exciter filter 13 and a barrier filter 22 are inserted in the optical path.

A CPU 12 receives signals from an operation unit 23, and performs control such as turning the lamp 1 on and off, inserting and removing the filters 2, 13, 22 in accordance with an imaging mode, activating the strobe lamp 4 synchronized to the operation of the shutter 34, exchanging the variable power lenses 14, 14', inserting and removing the return mirror 16, and the like. In addition, the CPU 12 receives the clock from a timer 21 activated when fluorescent imaging begins, the positional information of the focusing lens 15, and the like, and determines the imaging mode based on the signals from the operation unit 23, the shutter 34, the timer 21, and the like. For example, if the filter 2 is inserted, then it determines that the imaging mode is a special imaging mode (e.g., infrared fluorography); if the exciter filter 13 and/or the barrier filter 22 is inserted, or if the timer 21 is activated, then it determines that the imaging mode is the fluorography mode; and if the variable power lenses 14, 14' are exchanged, then it determines that the imaging mode is the variable power imaging mode. The type of imaging mode thus determined is then sent to an image processing unit 40. Furthermore, the CPU 12 controls the activation of the CCD camera 31.

In accordance with the imaging mode and the imaging conditions, the image processing unit 40 performs appropriate image processing of the fundus image obtained by the CCD camera 31. The processed fundus image is stored in a data recording and storage unit 41 in association with identification number of the subject eye, and is displayed on a display unit 50.

The display unit 50 comprises a touch screen 51 serving as specifying means 51. As discussed later, when deriving the actual distance between two points on a retina of the fundus, this screen is touched to specify the locations corresponding to those two points.

In addition, a data input unit 43 is provided that enables the user to enter subject eye parameters such as the diopter of the subject eye, the eye axial length, and the corneal radius of curvature. This is performed using a keyboard while viewing the screen, as is similar to an operation for inputting data into a database. Various information related to the ocular fundus can be loaded into the data recording and storage unit 41 via a network 44, or can be supplied from the data recording and storage unit 41 to the network 44.

A calculation unit 42 calculates the actual distance between two specified points based on data such as indications of the points on the touch screen, the inputted data, the imaging conditions, the type of fundus camera, and the like. The calculated data along with other data associated with the fundus image is stored in the data recording and storage unit 41 in association with the identification number of the subject eye.

Generally, if the imaging magnification is known (or if it is fixed), then the actual distance between two points on an ocular fundus can be known immediately from the taken image. However, for the case of measuring the distance between two points on a retina of the fundus, the subject eye forms part of the optical system, and the imaging magnification thus depends upon the individual differences of the subject eye. The makes the precise measurement of the distance on the retina image difficult.

The individual differences originate from the diopter of the subject eye, the eye axial length of the subject eye, and the corneal curvature of the subject eye. To perform accurate measurement, it is therefore necessary to know these factors for each subject eye. These three factors are mutually related, i.e., if two of them are known, then the remaining one can be derived. Therefore, ray tracing (simulation by computer) is used with a model eyeball to provide a table as shown in FIG. 2 for storing the radius of curvature of the frontal corneal surface with respect to the diopter of the subject eye and the eye axial length. This table can be stored in the data recording and storage unit 41, for example.

Figure 3:
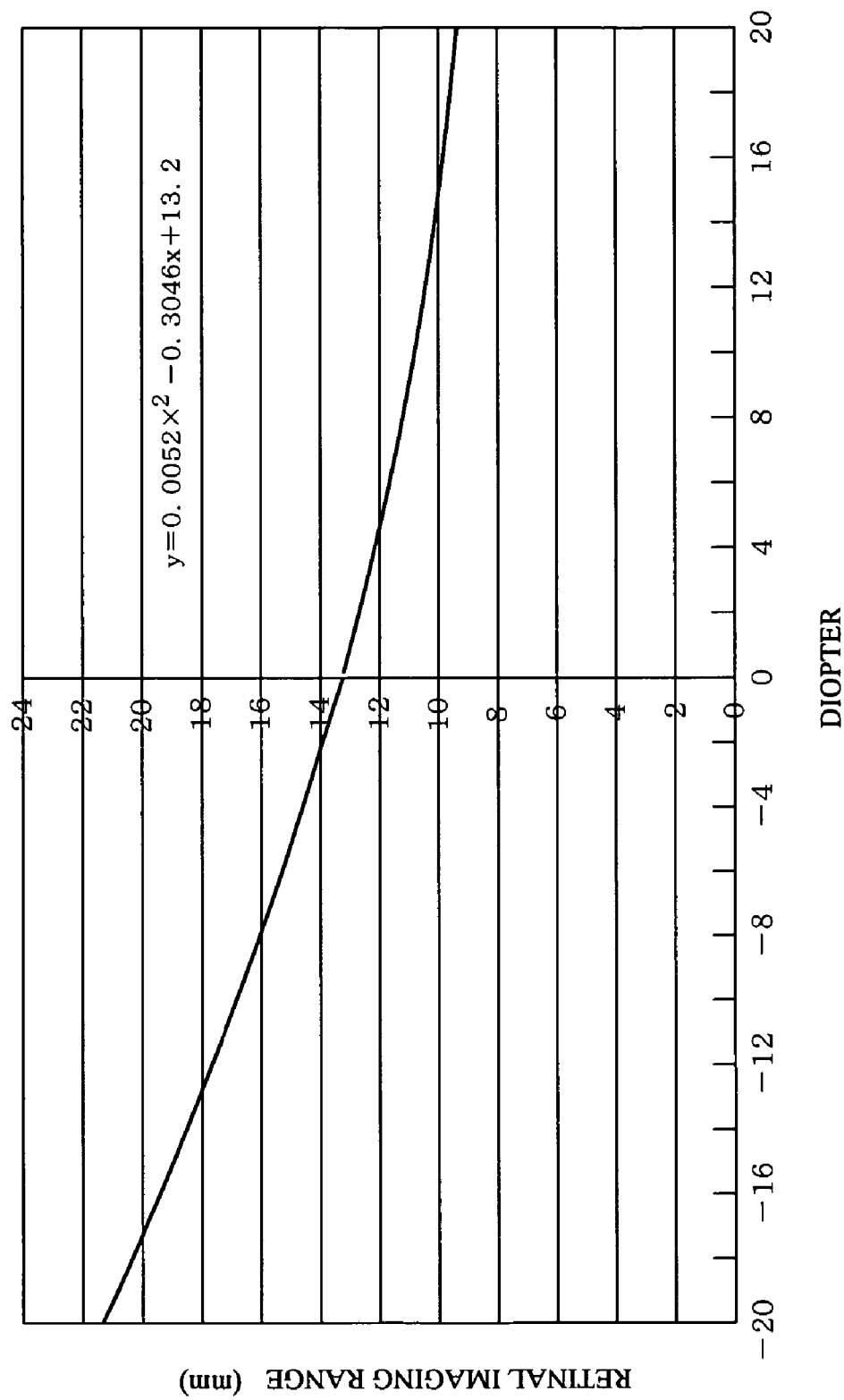
FIG. 3 is a graph that shows the relationship between the diopter and the retinal imaging range.

The magnification of the optical system of the imaging apparatus also depends upon the diopter of the subject eye. This is because the focusing lens 15 is moved for focus adjustment along the optical axis to compensate for the positional shift of the imaging position due to the diopter of the subject eye. If the imaging magnification changes, then the imaged range naturally changes. FIG. 3 shows a graph, showing that a retinal imaging range y varies as a diopter x changes and the magnification changes.

Figure 4:
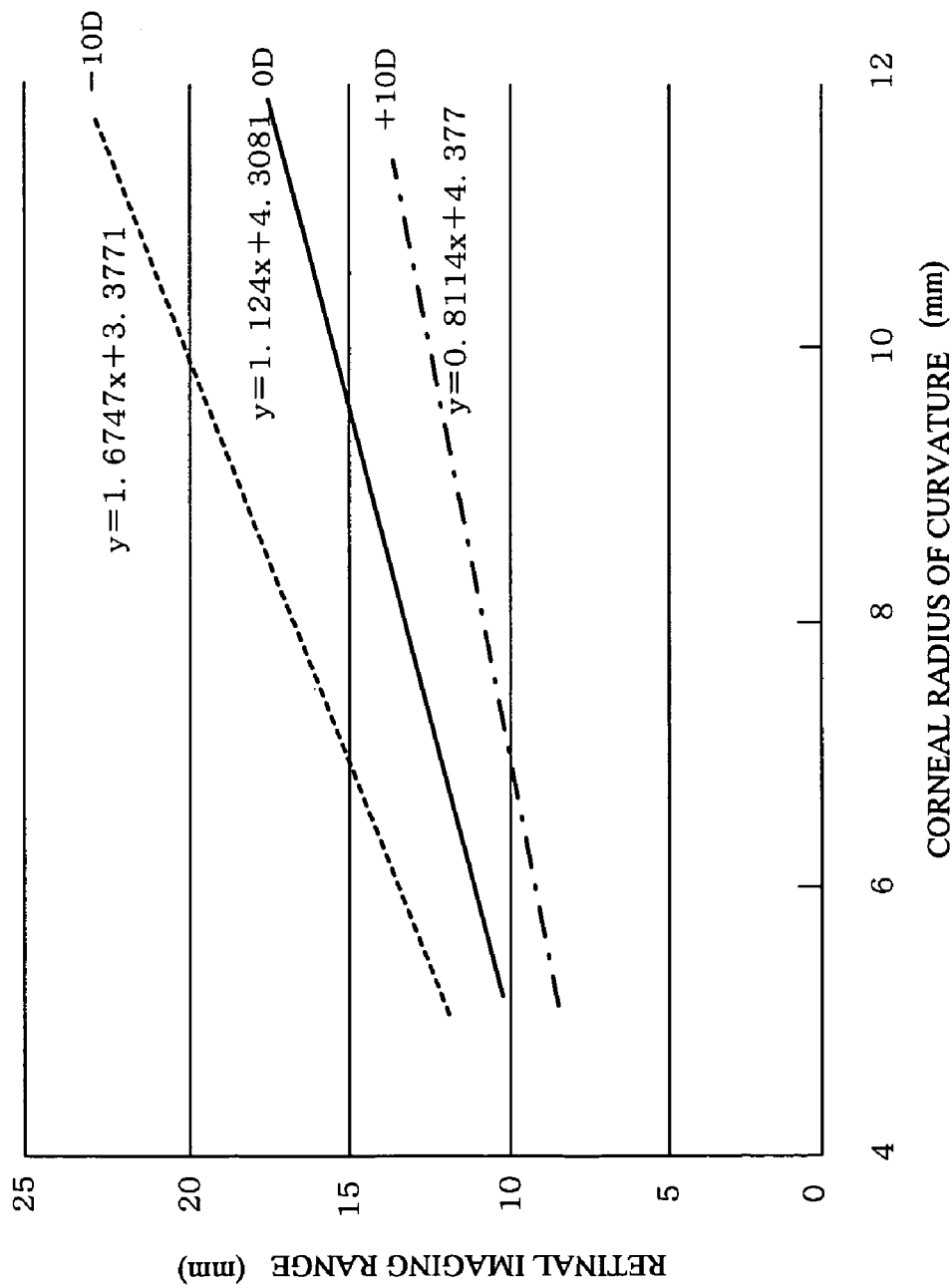
FIG. 4 is a graph that shows the association between the corneal radius of curvature and the retinal imaging range for each diopter.

The corneal radius of curvature and the eye axial length determine the diopter, but the corneal radius of curvature influences the imaging magnification and the imaging range, even if the diopter is the same. This relationship is shown in FIG. 4, which graphs the imaging range y with respect to the corneal radius of curvature x for three diopters, 0D (diopter=0) and ±10D (diopter=±10).

These variables are selectable in an optical design, and vary for each fundus camera. For example, if the fundus camera has a variable power function, then it is obvious that the imaging magnification will of course change.

According to the present invention, the actual distance on the ocular fundus is calculated using part or all of subject eye parameters of the diopter of the subject eye, the eye axial length of that subject eye, and the corneal curvature of the subject eye and using optical imaging parameters in the imaging optical system comprising the focusing lens 15, the variable power lenses 14 (14'), and the mask 32.

The imaging optical system includes optical imaging parameters such as the size of the mask 32, the imaging magnification produced by the movement of the focusing lens 15 along the optical axis, the variable power due to the variable power lenses 14 (14'), and the like. These parameters as well as the subject eye parameters such as the diopter, the eye axial length, and the corneal curvature determine the imaging range of the ocular fundus on the mask 32. The imaging range corresponds to the size of the mask image on the screen of the display unit, so that the calculation unit 42 calculates the actual distance on the ocular fundus between two specified points based on the imaging range of the ocular fundus, the coordinate distance of the mask image on the display screen, and the coordinate distance between the two specified points on the display screen.

To facilitate the calculation, a fundus camera of model A is used whose specifications, such as the mask size and the imaging magnification, are known beforehand. A model eyeball is also used with a virtual light source disposed on the mask. A retinal imaging range is derived by changing the diopter (diopter) and the eye axial length, and tracing a light source image on the retina by ray tracing. As shown in FIG. 5, these data are stored in the data recording and storage unit 41 in table format. This table shows that the imaging range of the retina is 13.07 mm (corresponding to the size of the mask on the retina) for the case of a fundus camera of model A having a prescribed mask size and an imaging magnification (equivalent to an angle of view of 50 degrees) and for the case of the diopter "0" and the eye axial length "24 mm" of the subject eye. The mask 32 appears on the display unit 50 in FIG. 7 as a mask image 32', and it can therefore be seen that the actual distance on the retina of a diameter d1 of the mask aperture is 13.07 mm.

It is preferable to prepare a table as shown in FIG. 5 for each fundus camera model, and to store such in the data recording and storage unit 41.

The following explains the method for deriving the actual distance between two points of a fundus image on a screen for the case of three examples: a first example wherein the diopter and the eye axial length of an affected eye are known; a second case wherein the diopter and the corneal curvature of an affected eye are known; and a third case wherein the diopter of the affected eye is unknown.

The diopter of the affected eye is previously measured by a refraction examination apparatus (an auto refractometer), and the like, and the eye axial length is previously measured by an ultrasonic diagnostic apparatus (A mode), and the like. If those variables are stored in a database in the data recording and storage unit 41 in association with identification information (ID number and left eye/right eye) of the subject eye, then they are read out from the subject eye identification information inputted via a data input apparatus. On the other hand, if not stored in a database, then the measured diopter and eye axial length are directly inputted from the data input unit 43.

The imaging magnification depends upon apparatus model and the magnification fluctuates due to the diopter. This influences the imaging range of the fundus image (the mask size on the fundus image). Therefore, a table as shown in FIG. 5 is stored for each model in the data recording and storage unit 41, as discussed above. The model of the fundus camera used is entered from the data input unit 43 to read the table corresponding thereto. The calculation unit 42 then derives the imaging range based on the diopter and the eye axial length of the subject eye.

Figure 6:
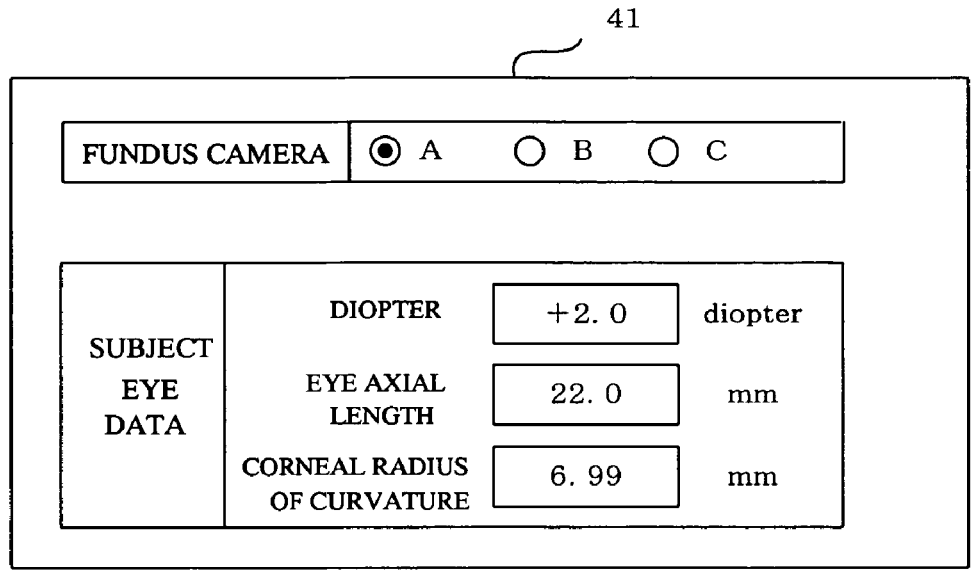
FIG. 6 is a dialogue box that shows the data input screen.
Figure 7:
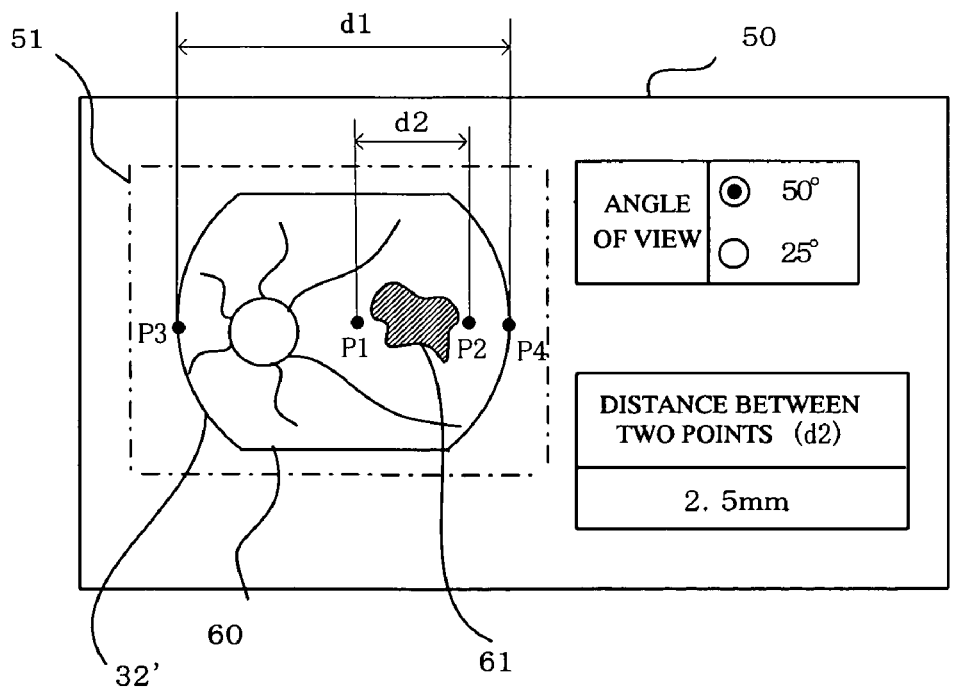
FIG. 7 is a dialogue box at a time when deriving the actual distance on an ocular fundus between two specified points on an ocular fundus.

For example, if a fundus camera type of A, a diopter of +2.0 and an eye axial length of 22.0 mm are input, as shown in FIG. 6, then an imaging range of 11.87 mm on the retina is obtained from FIG. 5. The value of this retinal imaging range corresponds to the actual distance of the diameter d1 of the mask image 32' in FIG. 7. If two points P1, P2 in the vicinity of a lesion part 61 of a fundus image 60 are specified via the touch screen 51, then the calculation unit 42 calculates a coordinate distance d2 between the two points P1, P2 based on the coordinate values thereof, and derives the coordinate distance d1 corresponding to the diameter thereof based on specified points P3 and P4 of the mask image. The calculation unit 42 can derive the actual distance of d2 by performing a proportional calculation based on the ratio between d1 and d2 and the actual distance of d1 (11.87 mm). In FIG. 7, that actual distance of 2.5 mm is displayed on the display unit 50, and this derived actual distance between the two points P1, P2 on the retina is stored in the data recording and storage unit 41 along with the image information that specifies the prescribed points and the coordinate information of the prescribed points P1, P2 on the image, and the like.

In the second example where the affected eye diopter is already known but the eye axial length is not known, there is the case wherein the corneal curvature is already known by the results of measurement, such as by using a keratometer. In such a case, data of the type shown in FIG. 2 is used that is stored in the data recording and storage unit 41. Based on this data, the table cell corresponding to the known corneal curvature is derived from the horizontal line of the diopter, and the eye axial length corresponding to that cell is read out. If the eye axial length is known, then the actual distance on the ocular fundus can be obtained from the distance between two prescribed points on the fundus image using the same method as in the first example.

However, in the case of the third example where the affected eye diopter is unknown, the diopter can be determined using the information at the time when the fundus camera is focused. In this case, a scale is provided on the adjustment knob of the focusing lens 15, and the diopter can be input by inputting the number during focusing, or by detecting and outputting the position of the focusing lens. If the eye axial length is already known, then the method the same as in the first example is used. If the corneal radius of curvature is already known, then the eye axial length is derived in accordance with the second example, and the actual distance on the ocular fundus is calculated in accordance with the first example.

Figure 8:
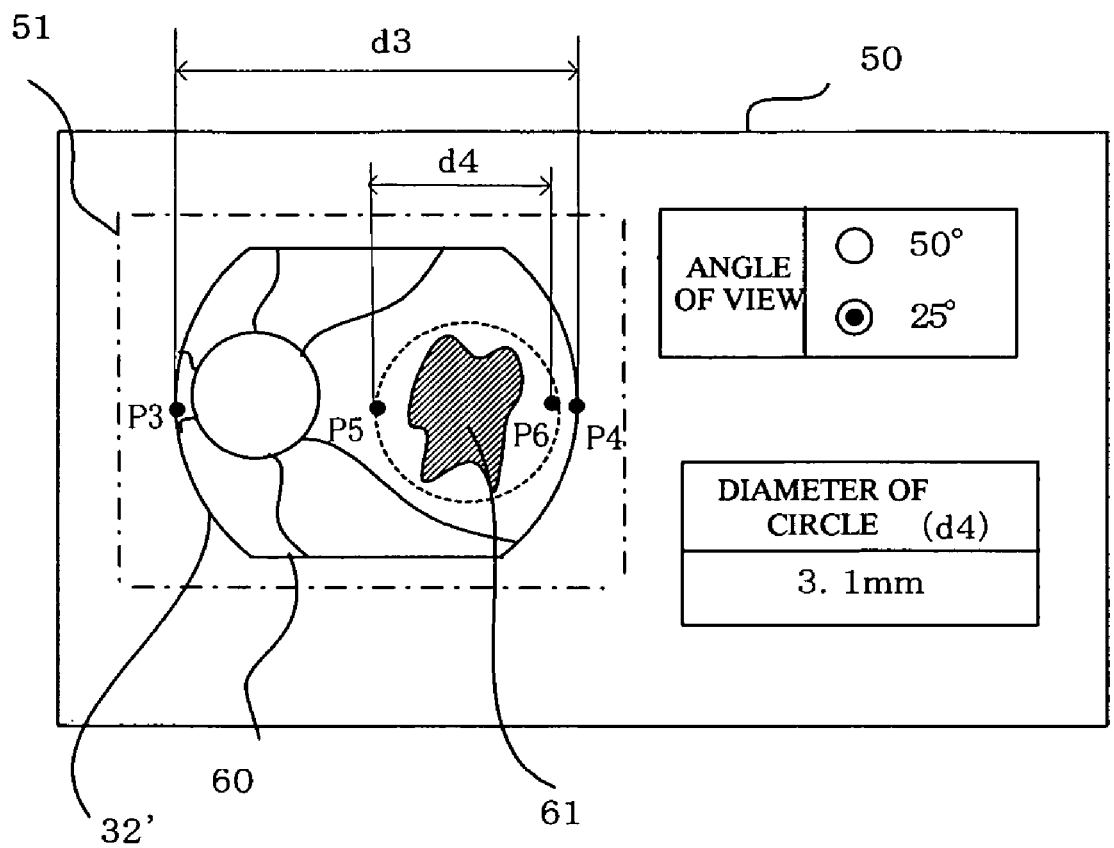
FIG. 8 is a dialogue box at a time when deriving the actual distance on an ocular fundus corresponding to the diameter of a drawn circle.

In the embodiments discussed above, a lesion part is specified by indicating two points by the touch screen 51; however, as shown in FIG. 8, a circle may be drawn around the lesion part 61 by a drawing means such as the CPU 12 or the calculation unit 42, and the actual distance on the ocular fundus corresponding to the diameter of that circle (distance d4 between P5, P6) may be calculated.

In the embodiment of FIG. 1, the focusing lens 15 may be controlled by an electric motor, such as a stepping motor, from the operation unit 23 via the CPU 12, instead of by manual control. In this case, the position of the focusing lens can be known even if a position detection mechanism is not provided.

The data input unit 43 is typically a keyboard that the operator uses to key in numerical values; however, if this is replaced by a system that is connected to another measuring instrument via the network 44, then the measurement results of other measuring instruments can be obtained as is from the network 44 and used in the calculations, or can be loaded from the data recording and storage unit 41 and used in the calculations.

In addition, the mask 32, the lens 33, and the CCD 31 are separately constituted; however, if the mask can be attached to the light receiving surface of the CCD 31, or if digital mask processing is performed, then the mask 32 and the lens 33 become unnecessary, and the light receiving surface of the CCD 31 can be placed at the position of the mask 32.

There would be no problem even if the prescribed point specifying means was not a touch screen system that specifies points directly on the screen, and instead is a means such as an ordinary mouse of the type seen with computers, or a means that conforms thereto.

Figure 9:
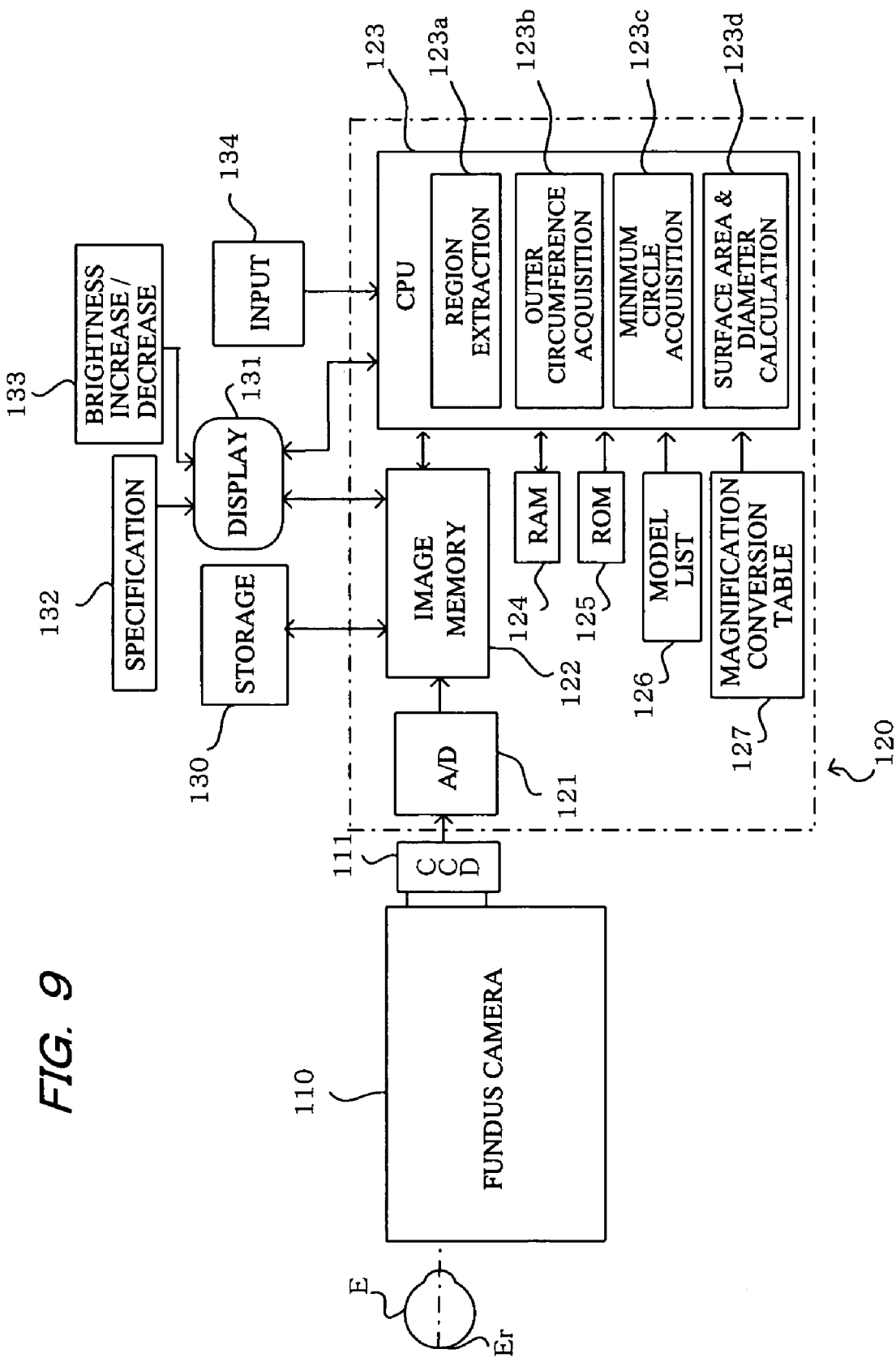
FIG. 9 is a block diagram showing the constitution of the ophthalmological measuring apparatus of the present invention.

FIG. 9 shows another embodiment of a fundus camera 110 that forms a fluorographic image of a fundus Er of an illuminated subject eye E onto an imaging device 111 such as a CCD, and the like. The fundus image fluorographically imaged by the imaging device 111 is input to an A/D converter 121 of an image processing apparatus 120. The fundus image is then converted to a digital signal by converting it to multivalue data in accordance with the A/D resolution, and is stored in an image memory 122.

The image processing apparatus 120 comprises a CPU 123 that performs various data processing and calculations. With the present invention, this CPU 123 functions as a region extracting means 123*a*, an outer circumference acquiring means 123*b*, a minimum circle acquiring means 123*c*, and a surface area and diameter calculating means 123*d*, and processes the fundus image by executing programs stored in a ROM 125, as discussed later. During this image processing, a RAM 124 is used as working memory that stores the inputted and processed data.

The image processing apparatus 120 is connectable to a storage apparatus 130, and can record and store in this storage apparatus 30 the fundus image taken by the fundus camera 110 and stored in the image memory 122. The fundus image stored by the storage apparatus 130 can be loaded into the image memory 122, and image processing can then be performed the same as if the fundus image came from the imaging device 111.

In addition, a displaying means comprising a monitor 131 and the like is connected to the image processing apparatus 120, and the fundus image stored in the image memory 122 and the processed fundus image are displayed on this monitor 131. A prescribed region or a prescribed point on the image displayed on the monitor 131 can be specified arbitrarily by a specifying means, such as a mouse 132. A brightness value increasing/decreasing means 133 is further provided that increases and decreases the brightness value (the brightness threshold value) of an image of a point on a screen specified by the mouse 132. Further, the image processing apparatus 120 is provided with an inputting means 134 such as a keyboard, a mouse, and the like to enter various data to the image processing apparatus 120.

The flow of processing will now be explained for measuring the size of a prescribed region, i.e., a lesion part, on a retina of a displaying means.

Image processing is performed by fluorographically imaging the fundus Er of the subject eye E with the fundus camera 110 onto the imaging device 111, converting that image to a digital signal by the A/D converter 121, storing that in the image memory 122 and displaying the fundus image on the monitor 131. Furthermore, the fluorographically imaged fundus image stored in the storage apparatus 130 can be loaded into the image memory 22 and processed for that purpose.

Figure 10A:
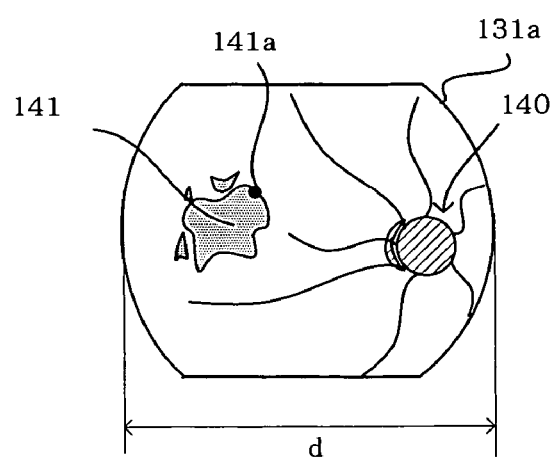
FIG. 10a through 10e are an illustrative view showing a flow when specifying the lesion part on the retina.
Figure 11A:
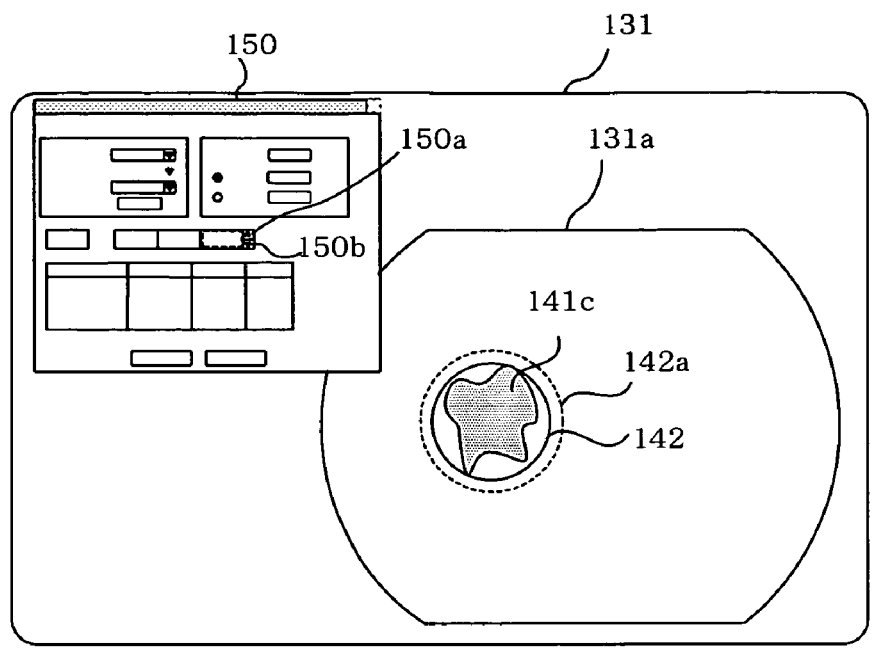
FIG. 11a through 11c are an illustrative view showing processes for deriving the laser irradiation region for irradiating the lesion part.
Figure 12:
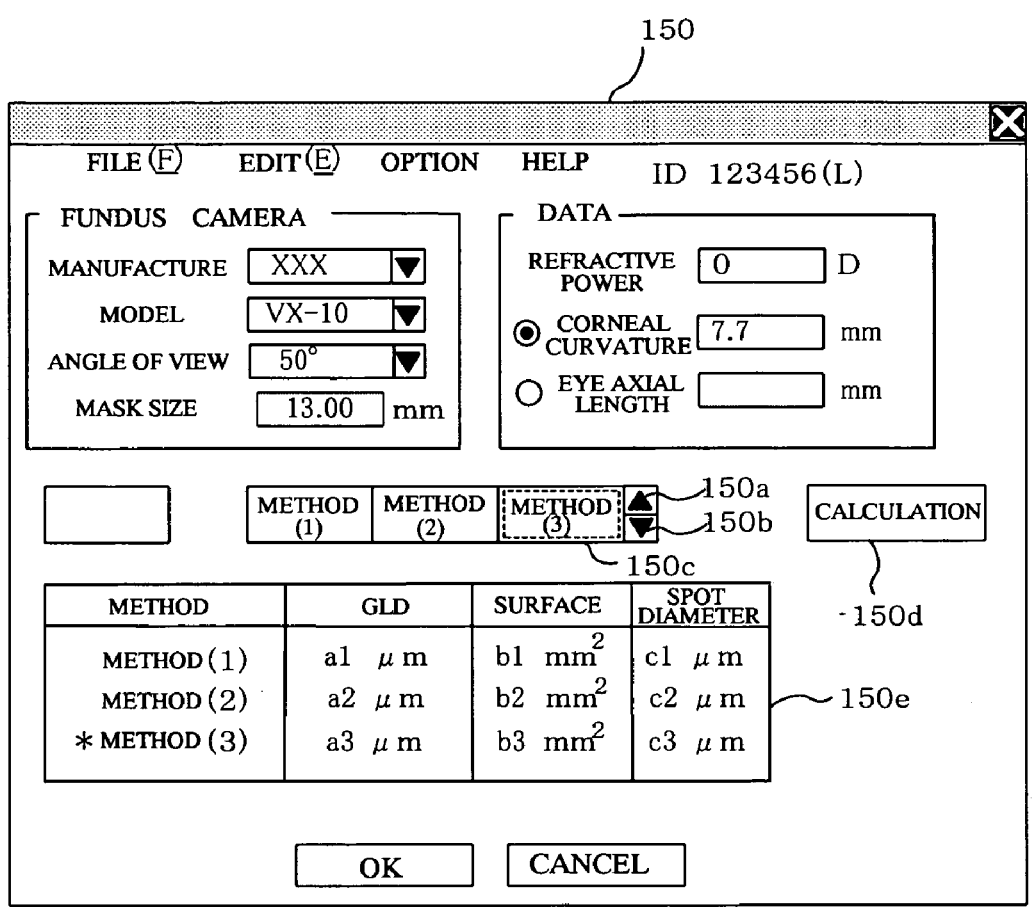
FIG. 12 is a screenshot of the dialog box displayed on the monitor.

The imaged or recorded fundus image on the monitor 131 is shown in FIG. 10*a*, and a dialog box 150 is also displayed in the upper left area on the monitor 131 as shown in FIG. 11*a*. FIG. 12 shows the dialog box 150 displaying the subject eye data including the ID number of the subject eye allocated to the fundus image, the left eye (L), the right eye (R), and the like; information about the fundus camera 110 (manufacturer, model); optical imaging parameters, such as the angle of view, the dimensions of the imaging mask, and the like; and parameters of the subject eye, such as the subject eye refractive power, the corneal curvature (keratometer), the eye axial length, and the like.

The manufacturer name of the fundus camera, the model name, the angle of view, and the size of the imaging mask are stored as a file in a fundus camera model list 126 for each fundus camera. When an ocular fundus is imaged by the fundus camera 110, the data associated with the fundus camera 110 is read from the fundus camera model list 126 and is automatically inputted into the various items of the dialog box 150. If the fundus image is loaded from the storage apparatus 130 and items have not yet been inputted, then the user inputs them via the inputting means 134.

If the fundus camera is specified and the abovementioned specifications are known, then a magnification conversion table 127 is loaded to derive therefrom a magnification conversion value.

The parameters of the subject eye, such as the refractive power of the subject eye, the corneal curvature (keratometer), and the eye axial length, are then input. It is preferable to display default values and have the user modify them. Note that the user can enter only one of the corneal curvature (keratometer) and the eye axial length.

The imaging mask determines the imaging range of the ocular fundus, and the image inside an imaging mask 131a in FIG. 10a and FIG. 11a corresponds to the fundus image. A well-known algorithm for deriving a minimum circle is used to automatically detect the imaging mask 131a and draw a circle that matches the imaging mask, and the pixel count of a diameter d thereof (FIG. 10a) is stored for later use.

The final image magnification is derived from the above-mentioned pixel count corresponding to the diameter d of the imaging mask, the mask size of the imaging mask specified by the dialog box 150, and the conversion value read from the above-mentioned magnification conversion table 127.

The user indicates the papilla edge to know where a laser beam should be irradiated. Conceivable methods include a method wherein the user specifies three or four points on the macula lutea of a papilla 140 and draws an arc by software, or a method wherein an oblong ellipse (a standard papilla size) is displayed on the screen and the user drags and moves that ellipse so that it is aligned with the papilla edge.

Figure 10B:
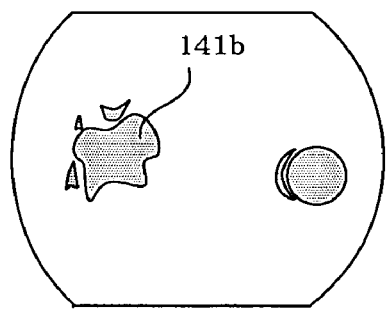

A lesion part 141 can be specified as follows: an arbitrary point, e.g., an outer edge part 141a of the lesion part 141, is first clicked by a mouse 132, as shown in FIG. 10a. The brightness value of the fundus image is converted to multivalue data (e.g., a value in the range of 0-256) by the A/D converter 121, so that the brightness value of the pixel of the clicked outer edge part 141a corresponds substantially to an intermediate value (e.g., 120) of the multivalue range, which is set as the threshold value for binary conversion. The region extracting means 123a then scans each pixel of the fundus image, and converts it to binary data such that pixels having a brightness value higher than the threshold are set to "1" and those below are set to "0", thereby extracting an image region having a brightness value higher than the threshold as shown in FIG. 10b.

Figure 10C:
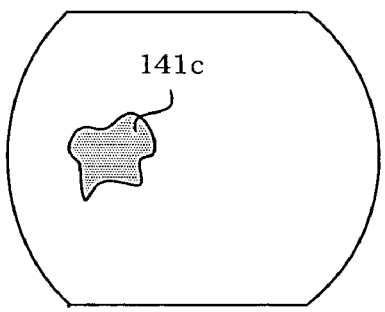
Figure 10D:
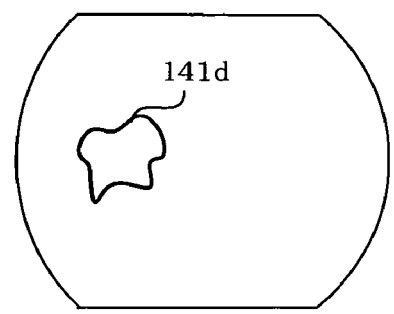
Figure 10E:
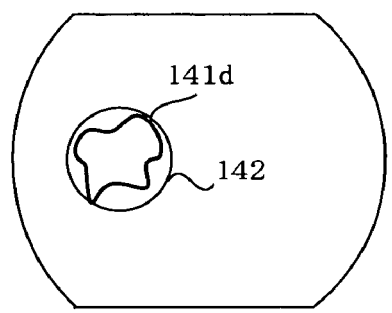

Because there is a plurality of regions having a brightness higher than the threshold value, narrowing is performed to select just the region that includes the position 141a clicked with the mouse 132. For this purpose, the outer circumference acquiring means 123b forms a 3×3 pixel region with its center at the clicked pixel and scans a region 141b therewith to select just a region 141c (FIG. 10c) by extracting the "1" pixel region. The thus selected region 141c is filtered to provide an outer circumference 141d of the region 141c as shown in FIG. 10d.

The minimum circle acquiring means 123c is then activated to acquire a minimum circle 142 that includes the entire outer circumference 141d in accordance with a well-known algorithm.

This method corresponds to a lesion part specifying method when operating a "Method (3)" button 150c in FIG. 12, but the lesion part can also be specified by selecting the other well-known "Method (1): User specifies two points thought to be the maximum diameter of the affected part" or the "Method (2): User specifies the region using a mouse operation to trace the outer circumference of the affected part."

After the minimum circle that includes the lesion part was acquired, the surface area and diameter calculating means 123d is activated by operating a "Calculation" button 150d in FIG. 12 to calculate a GLD (maximum diameter) corresponding to the diameter of the minimum circle, the surface area of the minimum circle, and the irradiation diameter of the laser beam that corresponds to the diameter of the minimum circle plus a margin of 1 mm. When calculating the surface area of the minimum circle and/or the diameter thereof (corresponding to the GLD), that calculated value is compensated in accordance with optical imaging parameters, such as the imaging magnification of the imaging optical system, the dimensions of the imaging mask, the position of the focusing lens in the optical axis direction, and the like, and is also compensated in accordance with subject eye parameters such as the refractive power.

The calculation results are displayed as shown in a lower part 150e in FIG. 12 together with the region of the specified lesion part 141c, the calculated minimum circle 142, and an irradiation diameter 142a of the laser beam, as shown in FIG. 11a. At that time, the image magnification is used to convert 1 mm to pixel count and draw the irradiation diameter. If the distance of the irradiation closest to the previously obtained papilla edge is less than 200 mm, then there is a risk that the papilla will be mistakenly irradiated, and a warning is therefore displayed by drawing the irradiation diameter in red.

In the example discussed above, the brightness threshold value was determined in accordance with a position where the outer edge part 141a of the lesion part was initially clicked, so that the region of the lesion part or the size of the minimum circle depends upon where is clicked. Therefore, the user can change the threshold value to change the region of the lesion part or the minimum circle on the screen, and verify the validity of the acquired image or the data.

Figure 11B:
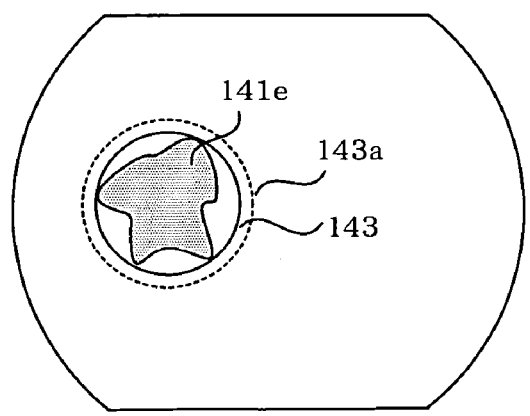

This is performed by, for example, operating increase/decrease buttons (brightness value increasing/decreasing means) 150a, 150b in the dialog box shown in FIG. 12. Each time the button 150b is clicked, the previously acquired brightness threshold value can be reduced in steps of a prescribed value; accordingly, the binary converted region of a lesion part 141e increases, and a drawn minimum circle 143 as well as an irradiation diameter 143a of the laser beam increases, as shown in FIG. 11b.

Figure 11C:
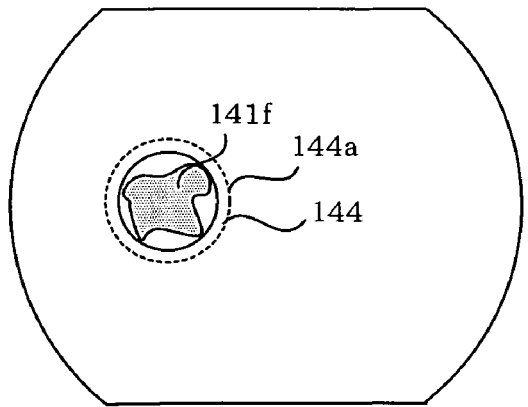

If, on the other hand, the button 150a is clicked, then the value of the previously acquired brightness threshold value can be increased in steps of a prescribed value with each click; thereby, the binary converted region of a lesion part 141f decreases, and a drawn minimum circle 144 as well as an irradiation diameter 144a of the laser beam decrease, as shown in FIG. 11c.

The brightness threshold value for binary conversion can thus be adjusted to change the size of the specified region of the lesion part. This allows the user to specify and select as the lesion part the region thought to be most appropriate while viewing the screen, and it is possible to easily specify the lesion part to be treated and to measure the actual distance on the retina thereof.

What is claimed is:

1. An ophthalmological measuring apparatus comprising:
    an imaging optical system for imaging a digital image of an ocular fundus with a mask disposed at the position conjugate to the ocular fundus to determine an imaging range thereof;
    means for displaying the imaged digital image;
    means for specifying points on the image displayed;
    storage means for storing the size of the mask on the ocular fundus that is calculated at least in accordance with subject eye parameters that affect the imaging magnification; and
    means for calculating an actual distance between the specified points on the ocular fundus based on the mask size that is read out from the storage means, a coordinate distance of the mask on a display screen, and a coordinate distance between the specified points on the display screen.

2. An ophthalmological measuring apparatus as set forth in claim 1, wherein the size of the mask on the ocular fundus is calculated in accordance with the diopter of the subject eye, the eye axial length of the subject eye, or the corneal curvature of the subject eye, or a combination thereof.

3. An ophthalmological measuring apparatus as set forth in claim 2, wherein the mask size on the ocular fundus is calculated for each diopter of the subject eye and eye axial length of the subject eye, taking into consideration optical imaging parameters in the optical imaging system.

4. An ophthalmological measuring apparatus as set forth in claim 1, wherein the mask size on the ocular fundus is calculated using a model eyeball.

5. An ophthalmological measuring apparatus as set forth in claim 1, wherein the relationship between the diopter of the subject eye, the eye axial length of the subject eye, and the corneal curvature of the subject eye is calculated in table format using a model eyeball, and, based on any two pieces of information from said table, another one piece of information is derived.

6. An ophthalmological measuring apparatus as set forth in claim 1, wherein the points specified correspond to those on the diameter of a circle drawn on the displayed image.

7. An ophthalmological measuring apparatus comprising:
displaying means for displaying a digital image of an imaged ocular fundus of a subject eye;
specifying means for specifying an arbitrary point on the displayed digital image; and
extracting means for extracting from the displayed digital image an image region whose brightness value is higher than a brightness value of the specified arbitrary point.

8. An ophthalmological measuring apparatus as set forth in claim 7, further comprising means for increasing or decreasing the brightness of the specified arbitrary point.

9. An ophthalmological measuring apparatus as set forth in claim 7, further comprising processing means for processing the image of the extracted image region to derive therefrom an outer circumference of the image region.

10. An ophthalmological measuring apparatus as set forth in claim 9, further comprising acquiring means for acquiring a minimum circle that includes the derived outer circumference of the image region.

11. An ophthalmological measuring apparatus as set forth in claim 10, further comprising means for calculating a surface area or a diameter of the acquired minimum circle and for compensating the calculated surface area or the diameter of the acquired minimum circle in accordance with optical imaging parameters.

12. An ophthalmological measuring apparatus as set forth in claim 11, wherein the optical imaging parameters include at least one of an imaging magnification of the imaging optical system, a dimension of an imaging mask, and a position of a focusing lens along an optical axis thereof.

13. An ophthalmological measuring apparatus as set forth in claim 10, further comprising means for calculating a surface area or a diameter of the acquired minimum circle and for compensating the calculated surface area or the diameter of the acquired minimum circle in accordance with subject eye parameters that affect the imaging magnification.

14. An ophthalmological measuring apparatus comprising:
an imaging optical system for imaging a digital image of an ocular fundus of a subject eye with a mask disposed at a position conjugate to the ocular fundus to determine an imaging range thereof;
a display screen that displays the digital image of the ocular fundus;
specifying means for specifying two points on the digital image of the ocular fundus displayed on the display screen;
first calculating means for calculating a size of the mask on the ocular fundus in accordance with subject eye parameters; and
second calculating means for calculating a distance between the specified two points on the displayed digital image of the ocular fundus in accordance with the calculated mask size, a coordinate distance of the mask on the display screen, and a coordinate distance between the two specified points on the display screen.

15. An ophthalmological measuring apparatus as set forth in claim 14; wherein the first calculating means calculates the size of the mask in accordance with at least one or a combination of a diopter of the subject eye, an axial length of the subject eye, and a corneal curvature of the subject eye.

16. An ophthalmological measuring apparatus as set forth in claim 15; wherein the first calculating means calculates the size of the mask using a model eyeball.

17. An ophthalmological measuring apparatus as set forth in claim 14; wherein the specified points correspond to those on a diameter of a circle drawn on the displayed digital image of the ocular fundus.

18. An ophthalmological measuring apparatus as set forth in claim 14; further comprising storage means for storing the size of the mask calculated by the first calculating means.

19. An ophthalmological measuring apparatus as set forth in claim 18; wherein the second calculating means calculates the distance between the specified two points on the displayed digital image of the ocular fundus in accordance with the mask size that is read out from the storage means.

* * * * *